US00PP31044P2

(12) United States Plant Patent
Hansen

(10) Patent No.: US PP31,044 P2
(45) Date of Patent: Nov. 12, 2019

(54) ***VERONICA* PLANT NAMED 'WIZARD OF AHHS'**

(50) Latin Name: ***Veronica* hybrid**
Varietal Denomination: Wizard of Ahhs

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/932,904

(22) Filed: May 17, 2018

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./251, 226, 263.1
CPC ..... A01H 5/02; A01H 5/00; A01H 6/68
See application file for complete search history.

(56) References Cited

U.S. PATENT DOCUMENTS

PP16,414 P2 * 4/2006 Verschoor ..... A01H 5/02 Plt./251
PP29,581 P2 * 8/2018 Ault ..... Plt./251

OTHER PUBLICATIONS

BBBarns Availability Perennial Price & Availability Apr. 18, 2018, retrieved on Apr. 10, 2019, retrieved from the Internet at https://static1.squarespace .com/static/55f76dcee4b0922dfea0384a/t/5ad72e8d6d2a73214a79bf8e/1524051597346/BBBarns+Availability+April+18%2C+2018.pdf, pp. 1,12. (Year: 2018).*
Better Homes & Gardens *Veronica* Magic Show 'Wizard of Ahhs'—Speedwell 2017, retrieved on Apr. 10, 2019, retrieved from the Internet at https://www.bhg.com/shop/white-flower-farm-veronica-magic-show-wizard-of-ahhs-speedwell-peb140b04f3d72970c6b32db3b32e232b.html, one page. (Year: 2017).*

* cited by examiner

*Primary Examiner* — June Hwu

(57) ABSTRACT

The new and distinct cultivar of ornamental spike speedwell plant, *Veronica* 'Wizard of Ahhs', with tight compact habit and stiff, freely-branched, early flowering with upright spikes producing large violet-blue flowers and glossy, clean, deep-green foliage.

1 Drawing Sheet

Botanical classification: *Veronica* hybrid.
Variety denomination: 'Wizard of Ahhs'.

BACKGROUND OF THE INVENTION

The present invention relates to the new and distinct cultivar of spike speedwell, botanically known as *Veronica* hybrid 'Wizard of Ahhs', and hereinafter referred to as the cultivar 'Wizard of Ahhs' or the "new plant". The new plant was hybridized on Mar. 8, 2011 by the inventor at a wholesale perennial nursery in Zeeland, Mich., USA, with the unprotected, unreleased, proprietary hybrid known as K7-38-309 as the female parent and 'Blue Pixie' (not patented) as the male parent. The individual seedling that was ultimately named 'Wizard of Ahhs' was identified by the breeder code 11-06-10 throughout the trial period.

The new plant has been asexually propagated by shoot tip cuttings at the same nursery in the greenhouses in Zeeland, Mich., since the summer of 2013 with subsequent asexually propagated plants found to be identical to the original selection with all the same traits as the original seedling.

No plants of *Veronica* 'Wizard of Ahhs' have been sold or disclosed by this or any other name, in this country or anywhere in the world, prior to one year from the filing of this application, with the exception of that was sold or disclosed within one year of the filing of this application and which was either derived directly or indirectly from the inventor.

BRIEF SUMMARY OF THE PLANT

*Veronica* hybrid 'Wizard of Ahhs' is unique from all other spike speedwell known to the inventor. Several other cultivars may have some similar traits, but this is the only variety known by the inventor to have the following characteristic combinations that establish the new plant as unique:

1. Tight compact habit with spreading dense mats of foliage.
2. Thick upright spikes with numerous large flowers of violet-blue petals.
3. Early blooming period beginning the middle of June in Michigan and blooming for four to five weeks.
4. Glossy, clean, deep green foliage.

The closest comparison varieties to the new plant are 'Focus Pocus' U.S. Plant Pat. No. 23,853, 'Glory' U.S. Plant Pat. No. 18,932, 'Sunny Border Blue'(not patented), 'Goodness Grows' (not patented) and 'Atomic Violet' U.S. Plant Pat. No. 21,780. 'Hocus Pocus' is taller and produces a lighter violet purple flower. 'Goodness Grows' has a shorter habit and flowers that are more bluish in hue. 'Atomic Violet' is taller in habit with different colored flowers than the new plant. Both 'Sunny Border Blue' and 'Glory' are both taller in habit and not as deeply colored. The female plant is taller than the new plant with longer spikes. The male parent is slightly shorter in habit, and not as broad as the new plant. 'Twilight' U.S. Plant Pat. No. 16,414 begins flowering later in the season than the new plant, is slightly shorter and the flowers are not as deep blue-violet. 'Enchanted Indigo' U.S. Plant Pat. No. 26,603 is taller in habit, the foliage is not as deep green, vernalization is not required to flower and the flowers are deep violet-blue.

BRIEF DESCRIPTION OF THE DRAWINGS

The photograph of the new plant demonstrates the overall appearance and unique traits of 'Wizard of Ahhs' as a two-year-old plant grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
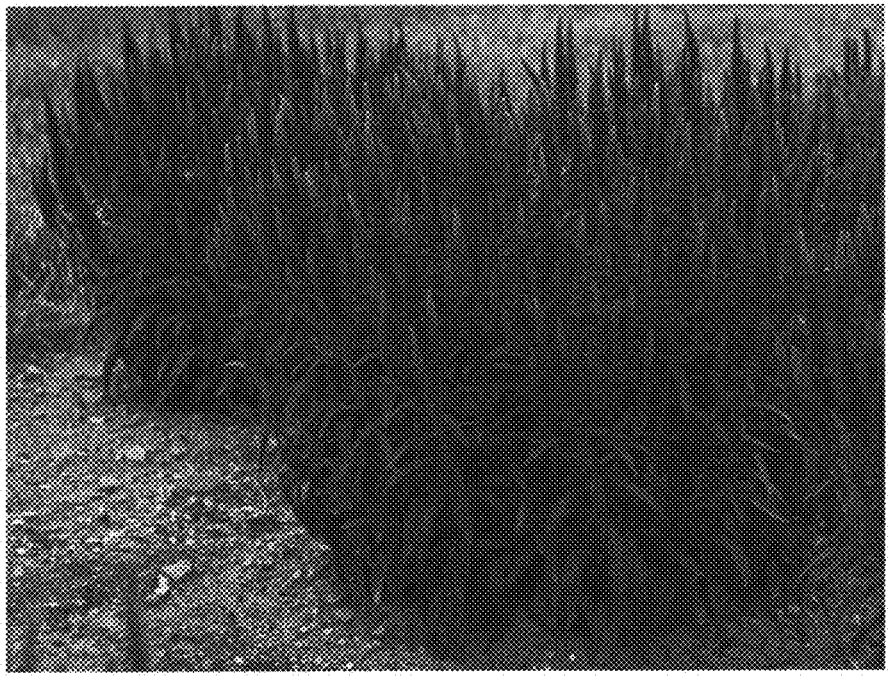
FIG. 1 shows the habit of the new plant in full flower.
Figure 2:
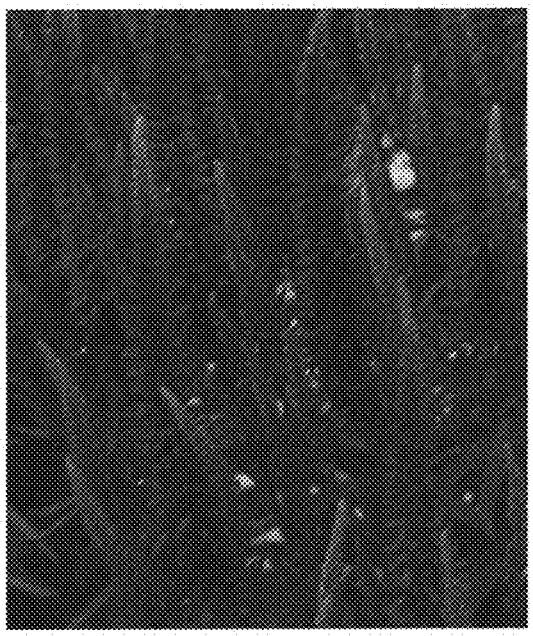
FIG. 2 shows a close-up of the flowers and buds.

The following descriptions and color references of *Veronica* 'Wizard of Ahhs' are based on the 2015 edition of The Royal Horticultural Society Colour Chart except where common dictionary terms are used. *Veronica* 'Wizard of Ahhs' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun trial garden of a nursery in Zeeland, Mich. with supplemental fertilizer and water as needed.

Botanical classification: *Veronica* hybrid;

Parentage: Female (seed parent) unprotected, unreleased, proprietary hybrid known only as K7-38-309; male (pollen parent) 'Blue Pixie';

Plant habit: Hardy herbaceous perennial, with average 30 branched stems, main stems blooming to about 38.0 cm tall and clumping to about 54 cm across; flowering beginning mid-June in Michigan and continuing for up to 5 weeks;

Propagation: The plant roots from cuttings in about 2 weeks and finishes to flowering in a 3.8 liter container in 8 to 10 weeks following a vernalization period of about 8 weeks;

Roots: Thin, fibrous, highly branched; color nearest RHS 161C;

Leaves: Simple, flat, elliptic to lanceolate; opposite; serrated margin with about 2 to 3 teeth per one centimeter; surface glabrous below and above, lustrous above, matte below; acute apex, attenuate base; to about 8.0 cm long by 2.0 cm wide decreasing in both length and width distally;

Leaf color: Mature leaves adaxial nearest RHS 137A, abaxial between RHS 137A and RHS 137B; young expanding leaves nearest RHS 143A adaxial and nearest RHS 144A abaxial;

Veins: Reticulate, abaxial finely puberulent, adaxial glabrate to glabrous; abaxial midrib costate;

Vein color: Adaxial midrib blend between RHS N144A and RHS 145C, secondary veins nearest RHS 137A; abaxial midrib nearest RHS 147C with secondary veins nearest RHS 137A;

Stem: Terete; young stems densely and finely puberulent, mature stems moderate density and finely puberulent; to about 33.0 cm long before flowers and about 3.0 mm diameter at base; freely branching at distal nodes; about 7 to 8 nodes before flowers; average internode length about 2.1 cm;

Stem color: Distally between RHS 138A and RHS 138B, proximally nearest RHS 138B blushed with nearest RHS 187C; nodes same color as remaining stem;

Petiole: Simple, slightly concaved upward on edges, margin sparsely ciliolate; about 1.0 cm long and 3.5 mm wide length shorter and narrower on distal leaves;

Petiole color: Adaxial nearest RHS 137A; abaxial between RHS 137A and RHS 137B;

Inflorescence: Terminal and lateral; triangular in bud becoming oblong;

Buds one to two days prior to opening: Convolute; narrowly oblong; acute apex; rounded base; about 8.0 mm long and 2.0 mm diameter near base;

Bud color: Nearest RHS 90A throughout;

Flowers: On heavily branched upright spikes in compressed conglomerate; numerous; zygomorphic; campanulate; approximately 200 per main spike and about 500 per stem with branches; about 10.5 mm long, about 7.0 mm across and 8.5 mm tall; flowers persist individually for 4 to 6 days whether on the plant or cut; petals self-cleaning, sepals and style persistent; flowering portion of terminal stem about 13.0 cm long and 3.0 cm wide;

Flower attitude: Mostly outwardly;

Flower timing: Beginning mid-June and continuing for about 4 to 5 weeks;

Flower fragrance: None detected;

Petals: Four; one larger petal above and three slightly smaller below and to either side; simple; margin entire; apex acute; fused in basal 2.5 mm to form corolla tube about 1.5 mm diameter; glabrous abaxial and pubescent with 1.0 mm long hairs in tufted band about 1.0 to 2.0 mm from adaxial base; upper larger petal with rounded apex, about 10.0 mm long and 4.0 mm wide; side and lower petals with acute apex, about 10.0 mm long and 3.0 mm wide;

Petal color: Abaxial nearest RHS 90A and adaxial nearest RHS 90A with hairs inside tube nearest RHS 91D; not changing with age; outer corolla tube distally nearest RHS 90A and between RHS 145C and RHS 145D in proximal 1.0 mm;

Androecium:

*Filaments*.—Two; divergent; glabrous; epipetalous about 1.0 mm from base; about 7.0 mm long by about 0.3 mm diameter; color nearest RHS 86A.

*Anther*.—Dorsifixed, longitudinal; elliptic with acute apex and rounded base; about 2.5 mm long and 1.0 mm across; color nearest RHS N92B.

*Pollen*.—Abundant, globose, less than 0.1 mm; nearest RHS 8C.

Gynoecium: Single, superior; persists after petal drop; about 10.5 mm long;

*Style*.—Straight; exserted; attitude mostly outwardly; about 9.0 mm long and 0.3 mm diameter; color nearest RHS 86A.

*Stigma*.—Globose; finely puberulent; about 0.3 mm in diameter; color nearest RHS 85C.

*Ovary*.—Spherical to slightly elliptic; puberulent distally and glabrous proximally; about 1.0 mm long and 0.8 mm in diameter; color nearest RHS 146C.

Calyx: Campanulate; about 4.0 mm long and 3.0 mm wide at apex;

Sepals: Four, surface dull, lanceolate to narrowly ovate, acute apex, basal 1.5 mm fused; sparsely ciliolate margin; adaxial glabrous; abaxial nearly microscopically puberulent; about 4.0 mm long and 1.5 mm across;

Sepal color: Adaxial nearest RHS 138B and abaxial nearest RHS 137B;

Peduncle: Strong, erect, branched at nodes; terete; puberulent; about 15 cm long and 2.5 mm in diameter at the base; attitude upwardly;

Peduncle color: Nearest RHS 138B;

Pedicel: Terete; rigid; about 1.0 mm long and 0.5 mm wide; finely puberulent; attitude mostly outwardly;

Pedicel color: Between RHS 137C and RHS 138B;

Bract: One, subtending each flower; linear; narrowly acute apex; margin entire; sessile; proximal bracts about 7.0 cm long and 1.0 mm wide decreasing in size distally;

Bract color: Adaxial between RHS 137A and RHS 139A, and abaxial nearest RHS 137A;

Fruit: Ellipsoid, about 3.0 mm long and 2.5 mm across; color between RHS 166A and RHS 166B;

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other spike speedwell has not been observed.

It is claimed:

1. A new and distinct cultivar of ornamental spike speedwell plant, *Veronica* 'Wizard of Ahhs', as herein described and illustrated.

* * * * *